United States Patent
George (10) Patent No.: US 11,730,472 B2
(45) Date of Patent: Aug. 22, 2023

(54) SURGICAL SYSTEM AND SURGICAL LOADING UNITS THEREOF

(71) Applicant: Covidien LP, Mansfield, MA (US)

(72) Inventor: Sabastian Koduthully George, Hyderabad (IN)

(73) Assignee: Covidien LP, Mansfield, MA (US)

( * ) Notice: Subject to any disclaimer, the term of this patent is extended or adjusted under 35 U.S.C. 154(b) by 250 days.

(21) Appl. No.: 16/812,596

(22) Filed: Mar. 9, 2020

(65) Prior Publication Data

US 2020/0337694 A1    Oct. 29, 2020

Related U.S. Application Data

(60) Provisional application No. 62/838,744, filed on Apr. 25, 2019.

(51) Int. Cl.
*A61B 17/068* (2006.01)
*A61B 17/072* (2006.01)

(52) U.S. Cl.
CPC ............ *A61B 17/0686* (2013.01); *A61B 2017/07257* (2013.01); *A61B 2017/07271* (2013.01); *A61B 2017/07285* (2013.01)

(58) Field of Classification Search
CPC ............ A61B 17/0684; A61B 17/0686; A61B 17/072; A61B 17/3423; A61B 2017/07207; A61B 2017/07257; A61B 2017/07271; A61B 2017/07278; A61B 2017/07285; A61B 2090/0801; A61B 2090/034
USPC ............................................ 227/175.1–182.1
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

European Search Report dated Sep. 29, 2020, issued in corresponding European Appl. No. 20171222, 9 pages.

*Primary Examiner* — Stephen F. Gerrity
*Assistant Examiner* — Linda J Hodge
(74) *Attorney, Agent, or Firm* — Carter, DeLuca & Farrell LLP (57) ABSTRACT

A surgical loading unit includes an anvil assembly, a staple cartridge assembly pivotably coupled to the anvil assembly, and a knife configured to approximate the staple cartridge assembly and the anvil assembly. The staple cartridge assembly has a staple cartridge chassis having a support protruding outwardly from a proximal end thereof. The knife includes an upper plate coupled to the staple cartridge chassis and a lower plate coupled to the anvil assembly. The support of the staple cartridge chassis has an upper surface that is coplanar with or above an upper surface of the upper plate when the knife is in a proximal position for preventing the knife from catching on a surgical port during use.

15 Claims, 4 Drawing Sheets

(56) References Cited

U.S. PATENT DOCUMENTS

| | | |
|---|---|---|
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |

(56) References Cited

U.S. PATENT DOCUMENTS

| | | |
|---|---|---|
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |

(56) References Cited

U.S. PATENT DOCUMENTS

| | | |
|---|---|---|
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Dasasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |

(56) References Cited

U.S. PATENT DOCUMENTS

| | | |
|---|---|---|
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0012704 A1 | 1/2010 | Tarinelli Racenet et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0053402 A1 | 3/2012 | Conlon et al. |
| 2012/0080336 A1 | 4/2012 | Shelton, IV et al. |
| 2012/0145767 A1 | 6/2012 | Shah et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0241499 A1 | 9/2012 | Baxter, III et al. |
| 2012/0253298 A1 | 10/2012 | Henderson et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0256376 A1 | 10/2013 | Barton et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0278765 A1 | 9/2016 | Shelton, IV et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049445 A1 | 2/2017 | Kostrzewski |
| 2017/0049452 A1 | 2/2017 | Milliman |
| 2017/0055981 A1 | 3/2017 | Vendely et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson, et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168649 A1 * | 6/2018 | Shelton, IV ........... A61B 34/30 |
| 2018/0168654 A1 | 6/2018 | Hodgkinson et al. |
| 2018/0214147 A1 | 8/2018 | Merchant et al. |
| 2018/0235626 A1 | 8/2018 | Shelton, IV et al. |
| 2019/0059896 A1 | 2/2019 | Beardsley |
| 2019/0183498 A1 * | 6/2019 | Shelton, IV ..... A61B 17/07207 |
| 2019/0290267 A1 | 9/2019 | Baxter, III et al. |

FOREIGN PATENT DOCUMENTS

| | | | |
|---|---|---|---|
| DE | 19924311 A1 | 11/2000 | |
| EP | 0327022 A2 | 8/1989 | |
| EP | 0594148 A1 | 4/1994 | |
| EP | 2130499 A1 * | 12/2009 | ....... A61B 17/07207 |
| EP | 2491867 A1 | 8/2012 | |
| EP | 3009080 A1 | 4/2016 | |
| JP | 2000166933 A | 6/2000 | |
| JP | 2002202213 A | 7/2002 | |
| JP | 2007124166 A | 5/2007 | |
| JP | 2010214132 A | 9/2010 | |
| WO | 9005489 A1 | 5/1990 | |
| WO | 95/16221 A1 | 6/1995 | |
| WO | 98/38923 A1 | 9/1998 | |
| WO | 9926826 A2 | 6/1999 | |
| WO | 0010456 A1 | 3/2000 | |
| WO | 0016684 A1 | 3/2000 | |
| WO | 2010075298 A2 | 7/2010 | |
| WO | WO-2016186905 A1 * | 11/2016 | ......... A61B 17/3462 |

* cited by examiner

SURGICAL SYSTEM AND SURGICAL LOADING UNITS THEREOF

CROSS-REFERENCE TO RELATED APPLICATIONS

The present application claims the benefit of and priority to U.S. Provisional Patent Application Ser. No. 62/838,744, filed on Apr. 25, 2019, the entire content of which is incorporated herein by reference.

BACKGROUND

Technical Field

The present disclosure relates generally to surgical instruments for endoscopic use and, more specifically, to surgical loading units of surgical instruments for stapling tissue.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include a surgical loading unit having an anvil assembly and a cartridge assembly for supporting an array of surgical staples, an approximation mechanism for approximating the cartridge and anvil assemblies, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Under certain procedures, a surgical port may be positioned within the small incision in the patient. During a procedure, the surgical loading unit may be inserted through the surgical port, and the small incision in the patient, to bring the surgical loading unit proximate a working site within the body of the patient. Such surgical ports provide pressure sealing during insufflation of the body cavity of the patient and may act as a guide channel for the surgical loading unit during insertion and actuation thereof.

SUMMARY

In accordance with an aspect of the present disclosure, a surgical loading unit is provided and includes an anvil assembly, a staple cartridge assembly, and a knife. The staple cartridge assembly is pivotably coupled to the anvil assembly and includes a staple cartridge chassis and a staple cartridge configured for receipt in a longitudinally-extending channel defined in the staple cartridge chassis. The staple cartridge chassis has a support protruding outwardly from a proximal end thereof. The knife includes an upper plate and a lower plate. The upper plate of the knife is coupled to the staple cartridge chassis and disposed outside of the channel. The upper plate has an upper surface and a lower surface. The lower plate of the knife is coupled to the anvil assembly. The knife is configured to move from a proximal position toward a distal position to pivot the staple cartridge chassis toward the anvil assembly. The support of the staple cartridge chassis has an upper surface that is coplanar with or above the upper surface of the upper plate when the knife is in the proximal position.

In aspects, the support of the staple cartridge chassis may be disposed alongside the upper plate of the knife when the knife is in the proximal position.

In some aspects, the staple cartridge chassis may define a longitudinally-extending slot. The support of the staple cartridge chassis may be disposed on both sides of the slot.

In other aspects, the support of the staple cartridge chassis may be disposed alongside a first lateral side of the upper plate of the knife and a second lateral side of the upper plate of the knife when the knife is in the proximal position.

In further aspects, the upper surface of the support of the staple cartridge chassis may be above the upper surface of the upper plate of the knife when the knife is in the proximal position.

In aspects, the knife may have a blade disposed between and interconnecting the upper and lower plates.

In some aspects, the support of the staple cartridge chassis may be monolithically formed with the proximal end of the staple cartridge chassis.

In accordance with another aspect of the present disclosure, a surgical system is provided and includes a surgical port and a surgical loading unit. The surgical port defines a guide channel therethrough and is configured to be positioned within a small incision in a patient. The surgical loading unit includes an anvil assembly, a staple cartridge assembly, and a knife. The staple cartridge assembly is pivotably coupled to the anvil assembly and includes a staple cartridge chassis and a staple cartridge. The staple cartridge chassis defines a longitudinally-extending channel and has a support protruding outwardly from a proximal end of the chassis. The staple cartridge is configured for receipt in the channel of the staple cartridge chassis. The knife includes an upper plate and a lower plate. The upper plate of the knife is coupled to the staple cartridge chassis and disposed outside of the channel. The upper plate has an upper surface and a lower surface. The lower plate of the knife is coupled to the anvil assembly. The knife is configured to move from a proximal position toward a distal position to pivot the staple cartridge chassis toward the anvil assembly. The support of the staple cartridge chassis has an upper surface that is coplanar with or above the upper surface of the upper plate of the knife when the knife is in the proximal position for expanding a portion of the guide channel of the surgical port out of a path of the knife.

In aspects, the support of the staple cartridge chassis may be configured to contact and raise an inner peripheral surface of the surgical port to a position coplanar with or above the upper surface of the upper plate of the knife. As such the knife is configured to pass under the inner peripheral surface of the surgical port during movement to the proximal position.

BRIEF DESCRIPTION OF THE DRAWINGS

Surgical instruments including embodiments of the presently disclosed adapter assemblies are disclosed herein with reference to the drawings, wherein.

DETAILED DESCRIPTION

Persons skilled in the art will understand that the adapter assemblies and surgical loading units specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term "distal" refers to that portion of the surgical instrument which is farthest from a clinician, while the term "proximal" refers to that portion of the surgical instrument which is closest to the clinician. In addition, as used herein, the term clinician refers to medical staff including doctors, nurses and support personnel.

Figure 1A:
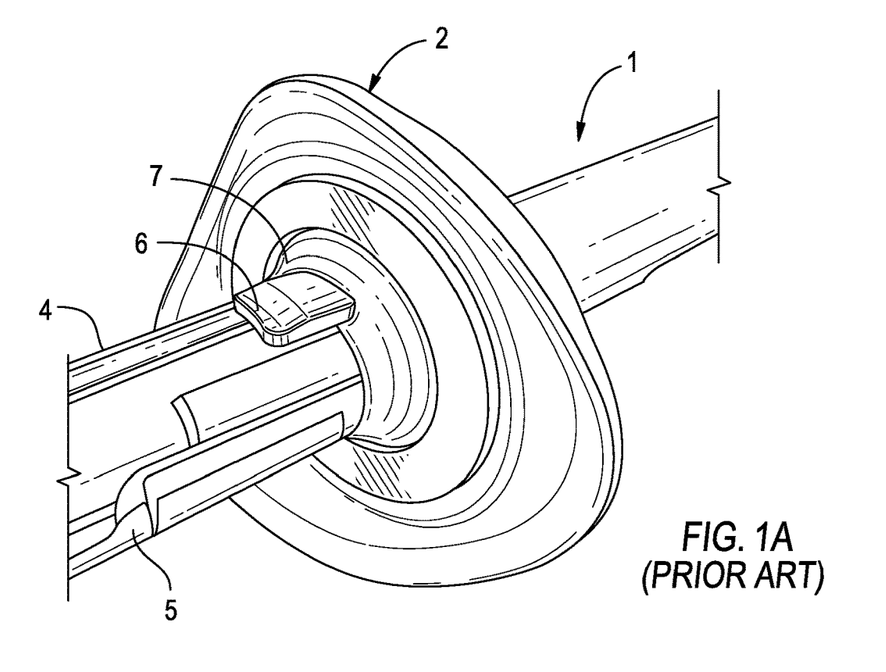
FIG. 1A is an enlarged perspective view of a prior art surgical loading unit illustrating a knife thereof caught on a surgical port.
Figure 1B:
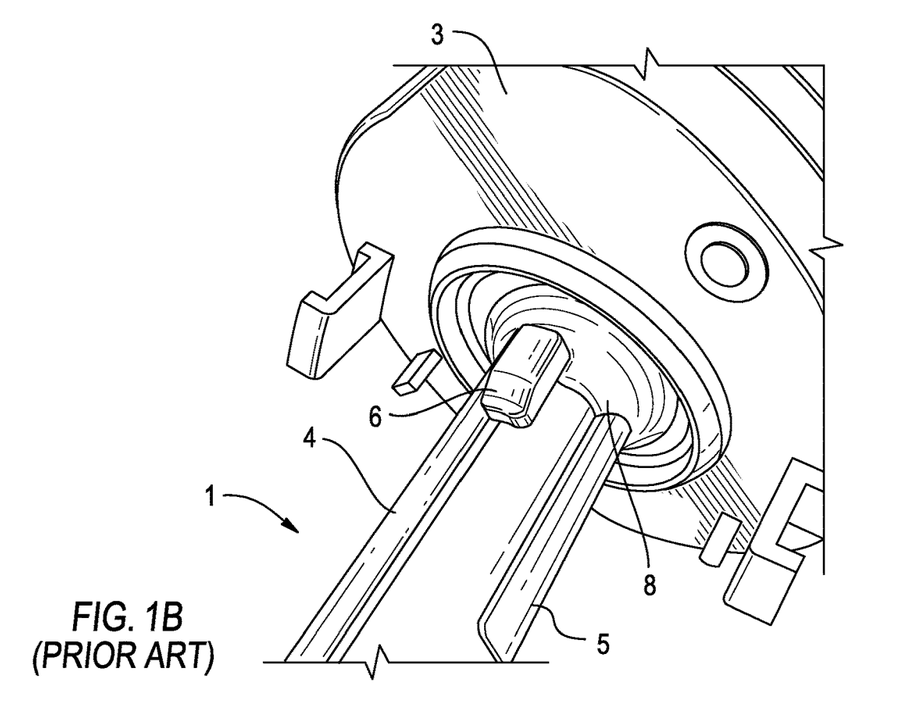
FIG. 1B is an enlarged perspective view of the prior art surgical loading unit of FIG. 1A illustrating the knife caught on another type of surgical port.

With brief reference to FIGS. 1A and 1B, a prior art surgical loading unit 1 is shown passed through a first type of surgical port 2 (FIG. 1A) and a second type of surgical port 3 (FIG. 1B). The surgical loading unit 1 has a staple cartridge assembly 4 pivotably coupled to an anvil assembly 5 and a knife 6 coupled to each. During advancement of the knife 6 from a proximal position, as shown in FIGS. 1A and 1B, to a distal position, the knife 6 pivots the staple cartridge assembly 4 toward the anvil assembly 5 while severing tissue disposed between the staple cartridge assembly 4 and the anvil assembly 5. After moving to the distal position, the knife 6 is retracted back toward the proximal position to reset. However, as shown in FIGS. 1A and 1B, an inner peripheral surface 7 or 8 of the respective surgical port 2 or 3 may get caught underneath an upper plate of the knife 6 inhibiting further actuation of the surgical loading unit 1 and/or removal of the surgical loading unit 1 from the surgical port 2 or 3.

The present disclosure provides a staple cartridge assembly with a feature that prevents the knife from catching on the surgical port during retraction of the knife. The staple cartridge assembly has a chassis through which the knife translates during actuation of the stapling function. As the knife moves to the retracted position, the knife passes under the surgical port due to a surface feature that protrudes from the outer surface of the chassis and raises the surgical port out of the path of the knife. In further aspects, the surgical loading unit may be provided with a sleeve that surrounds the knife without inhibiting its translation. The sleeve acts as a barrier between the surgical port and the knife to prevent the knife from catching on the surgical port. Additional advantages of the presently disclosed surgical loading units and components thereof are described below.

Figure 2:
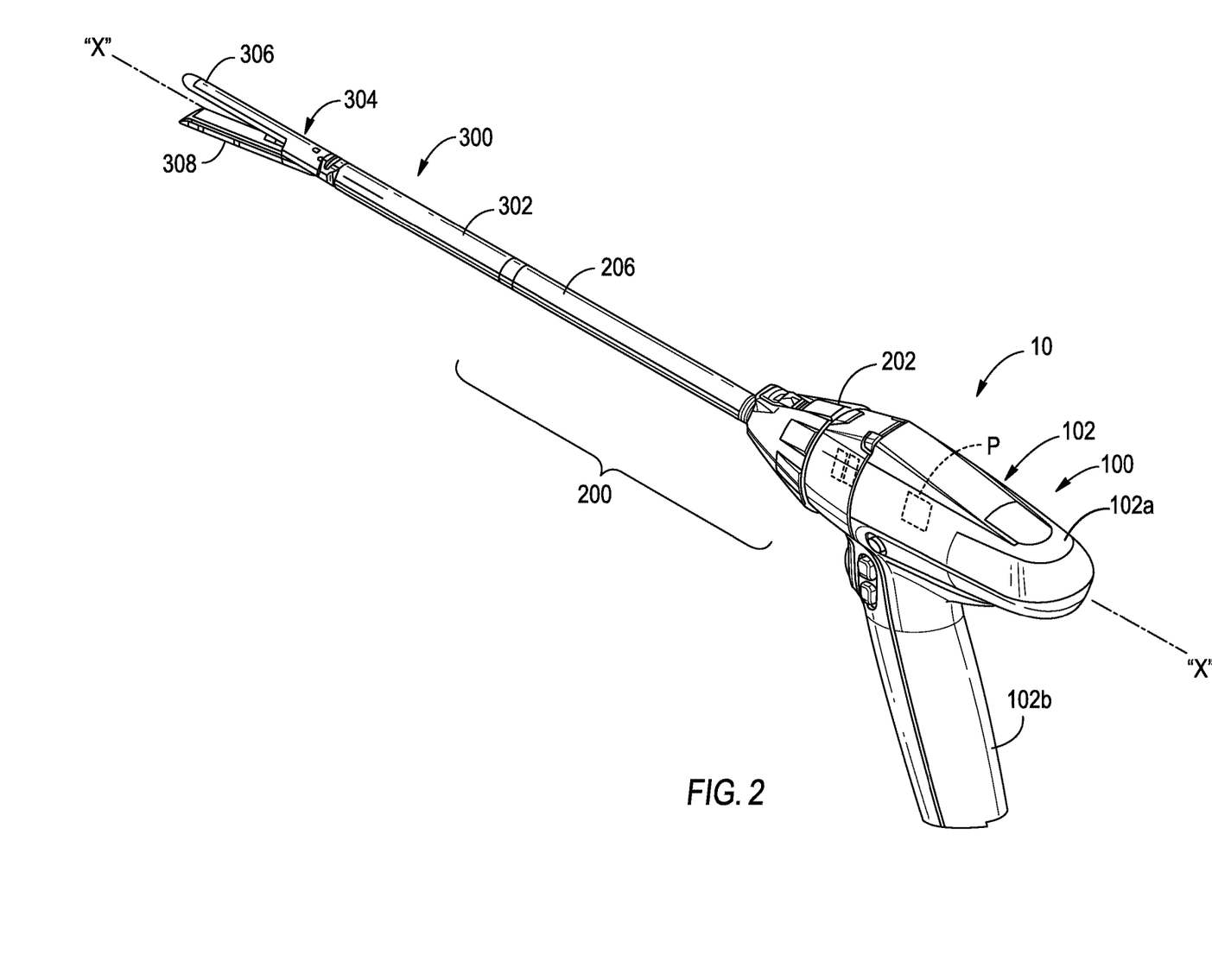
FIG. 2 is a perspective view of a surgical instrument including an adapter assembly in accordance with an embodiment of the present disclosure interconnected between an exemplary electromechanical handle assembly and a surgical loading unit.

With reference to FIG. 2, a surgical instrument, in accordance with an embodiment of the present disclosure, is generally designated as 10, and is in the form of a powered hand held electromechanical surgical instrument configured for clamping and/or sealing tissue. The surgical instrument 10 includes a handle assembly 100, an adapter assembly 200, and a surgical loading unit 300. The handle assembly 100 is configured for selective coupling, via the adapter assembly 200, to a plurality of different surgical loading units, such as, for example, the surgical loading unit 300. Each surgical loading unit is configured for actuation and manipulation by the powered handle assembly 100.

The handle assembly 100 includes a handle housing 102 having an upper housing portion 102a which houses various components of the handle assembly 100, and a lower hand grip portion 102b extending from the upper housing portion 102a. The lower hand grip portion 102b may be disposed distally of a proximal-most end of the upper housing portion 102a. Alternately, other handle configurations are envisioned. The handle housing 102 defines a cavity therein for selective removable receipt of a rechargeable battery (not shown) and receipt of a drive mechanism (not shown). The battery is configured to supply power to the electrical components of the surgical instrument 10. The cavity of the handle housing 102 has a processor "P" situated therein. The processor "P" is configured to control the various operations of the surgical instrument 10. The drive mechanism is configured to drive shafts and/or gear components in order to perform various operations of the surgical instrument 10. In particular, the drive mechanism is configured to drive shafts and/or gear components in order to selectively move an end effector 304 of the loading unit 300 relative to a proximal body portion 302 of the loading unit 300, to rotate the loading unit 300 about a longitudinal axis "X" relative to the handle assembly 100, to move/approximate an anvil assembly 306 and/or a cartridge assembly 308 of the loading unit 300 relative to one another, and/or to fire staples from within the cartridge assembly 308 of the loading unit 300.

While the depicted surgical instrument 10 may be configured to fire staples, it is contemplated that the surgical instrument 10 may be adapted to fire any other suitable fastener such as clips and two-part fasteners. Additionally, while the figures depict a linear surgical stapling instrument 10, it is envisioned that certain components described herein may be adapted for use in other types of endoscopic surgical instruments including non-linear surgical stapler loading units, endoscopic forceps, graspers, dissectors, other types of surgical stapling instruments, powered vessel sealing and/or cutting devices, etc.

Generally, the adapter assembly 200 of the surgical instrument 10 includes an outer housing 202 and an outer tube 206 extending distally from the outer housing 202. A proximal end of the outer housing 202 is configured to be operably coupled to the handle assembly 102 or, in other embodiments, a surgical robotic system (not shown) responsible for actuating the surgical instrument 10. The outer tube 206 has a proximal end portion fixed within the distal end portion of the outer housing 202. In other embodiments, the outer tube 206 may be rotatable relative to and within the outer housing 202. The surgical loading unit 300 is adapted to be attached to a distal end portion of the outer tube 206 of the adapter assembly 200 and may be configured for a single use, or may be configured to be used more than once.

The loading unit 300 is a disposable loading unit ("DLU") that is releasably secured to the outer tube 206 of the adapter assembly 200 and thus, replaceable with a new loading unit. The loading unit 300 may be a single use loading unit ("SULU") that is used one time and then replaced to facilitate multiples uses of the surgical instrument 10 on a patient. For example, during a surgical procedure, the surgical instrument 10 can be used to staple and cut tissue, and the entire SULU is replaced after each staple and cut operation of the surgical instrument 10. The loading unit 300 may be a multi-use loading unit ("MULU") that is re-useable a predetermined number of times. Alternatively, the loading unit 300 may be permanently affixed to the outer tube 206.

With reference to FIGS. 2-5, the surgical loading unit 300 generally includes a proximal body portion 302 and an end effector 304 coupled thereto. The end effector 304 has an anvil assembly 306, a staple cartridge assembly 308 pivotably coupled to the anvil assembly 304, and a knife 310 translatable through the end effector 304 to approximate the staple cartridge assembly 308 and the anvil assembly 306. The cartridge assembly 308 includes a carrier, such as, for example, a chassis 312 defining a longitudinally-extending channel 314. The channel 314 of the chassis 312 is dimensioned and configured to selectively receive a staple cartridge 316 therein. Corresponding tabs and slots (not explicitly shown) formed along the staple cartridge 316 and the chassis 312 function to retain the staple cartridge 316 within the chassis 312. The chassis 312 defines a central longitudinal slot 318 extending the length thereof to enable passage of the knife 310 therethrough. The slot 318 extends through an outer surface 320 of the chassis 312 to expose the slot 318 to the outside environment.

Figure 3:
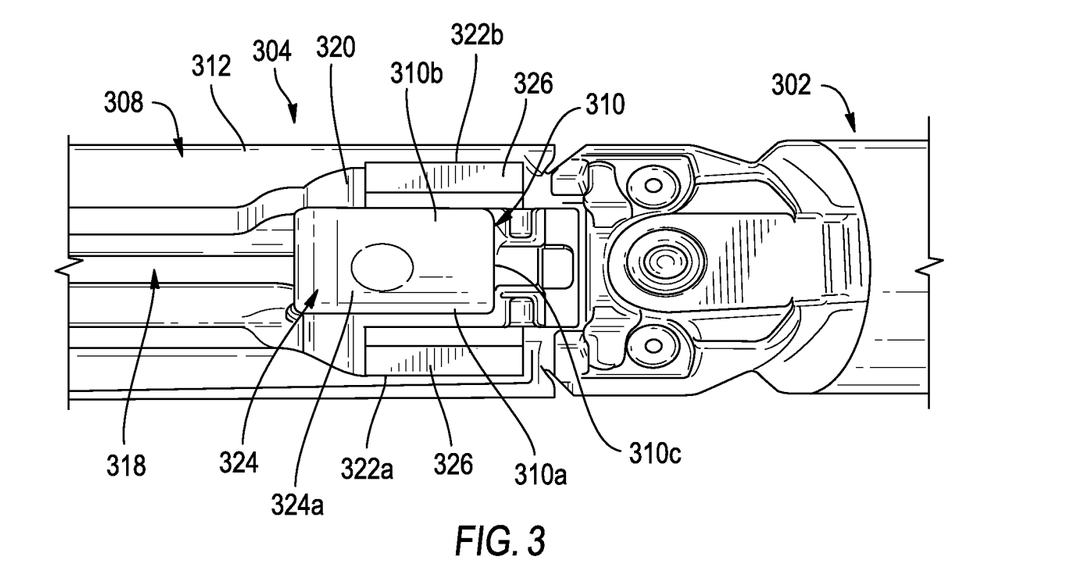
FIG. 3 is an enlarged top view of a staple cartridge assembly of the surgical loading unit of FIG. 2 illustrating an knife of the surgical loading unit in a proximal position and adjacent a pair of surgical port supports.
Figure 4:
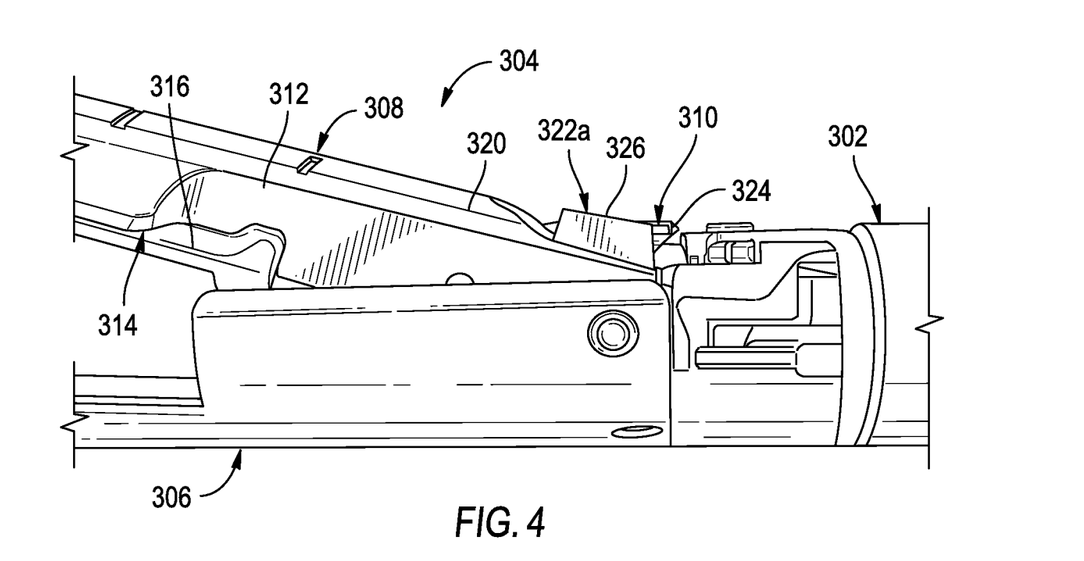
FIG. 4 is an enlarged side view of the staple cartridge assembly of FIG. 3 illustrating the surgical port support elevated above the knife.
Figure 5:
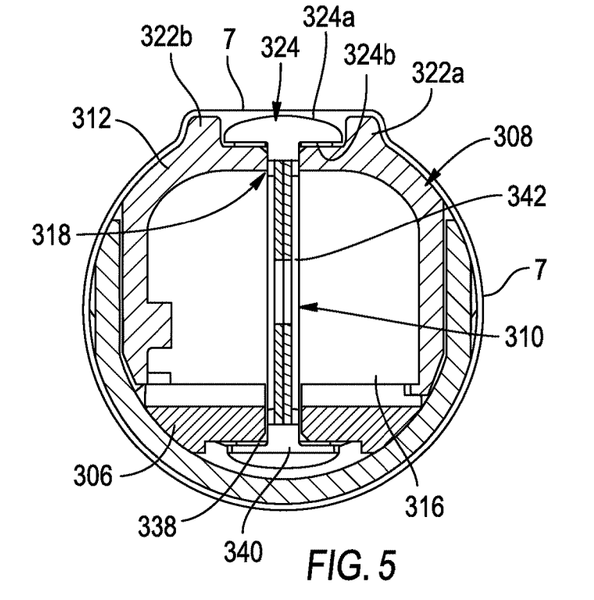
FIG. 5 is side cross-sectional view of the surgical loading unit of FIG. 2 with an inner peripheral surface of a surgical port disposed thereabout.

With reference to FIGS. 3-5, the proximal end of the chassis 312 has a pair of surgical port supports 322a, 322b disposed on opposite sides of the slot 318 in the chassis 312. The supports 322a, 322b are monolithically formed with the outer surface 320 of the chassis 312 and protrude upwardly therefrom a selected distance. In embodiments, the supports 322a, 322b may be connected with the outer surface 320 of the chassis 312 instead of being monolithically formed therewith. The supports 322a, 322b are elongated surface features having a length substantially equal to a length of the knife 310. In other aspects, the supports 322a, 322b may be protuberances having any suitable length. The supports 322a, 322b are respectively disposed laterally adjacent to opposing lateral edges or sides 310a, 310b of an upper plate 324 of the knife 310 when the knife 310 is in the proximal position. In some aspects, a proximal portion of each of the supports 322a, 322b may be disposed proximally of a proximal edge 310c of the upper plate 324 of the knife 310.

The supports 322a, 322b extend upwardly from the outer surface 320 of the chassis 312 a selected distance, such that an upper surface 326 of the supports 322a, 322b are aligned (e.g., coplanar) with an upper surface 324a of the upper plate 324 of the knife 310. In some aspects, the upper surface 326 of the supports 322a, 322b may extend slightly above the upper surface 324a of the upper plate 324 of the knife 310. In either aspect, with the surgical port (e.g., one of the surgical ports 2 or 3 shown in FIGS. 1A and 1B) positioned around the end effector 304 of the surgical loading unit 300, as shown in FIG. 5, as the knife 310 moves to the proximal position (FIGS. 3 and 4), the inner peripheral surface 7 or 8 of the surgical port 2 or 3 is supported above the path of the upper plate 324 of the knife 310 by the supports 322a, 322b to allow the knife 310 to pass underneath the inner peripheral surface 7 or 8 of the surgical port 2 or 3. Without the supports 322a, 322b lifting the inner peripheral surface 7 or 8 of the surgical port 2 or 3 substantially or completely out of the path of the upper plate 324 of the knife 310, the upper plate 324 could potentially pass over the inner peripheral surface 7 or 8 of the surgical port 2 or 3, which may result in knife 310 getting caught on the surgical port 2 or 3.

In some aspects, the supports 322a, 322b may be one support configured as a hood that extends from a first side of the slot 318 in the chassis 312, over the slot 318, to a second side of the slot 318, whereby the support extends over the knife 310 when the knife 310 is in the proximal position. The hood-like support may have an arcuate configuration, a squared configuration, or any other suitable configuration. In even further aspects, instead of or in addition to using supports 322a, 322b, the surgical loading unit 300 may be provided with a flexible, tubular sleeve (not shown) that surrounds the proximal end of each of the staple cartridge assembly 308 and the anvil assembly 306. The sleeve covers the upper plate 324 of the knife 310 without inhibiting its translation therethrough and acts as a barrier between the surgical port 2 or 3 and the knife 310 to prevent the knife 310 from catching on the surgical port 2 or 3 as it moves to the proximal position.

Figure 6:
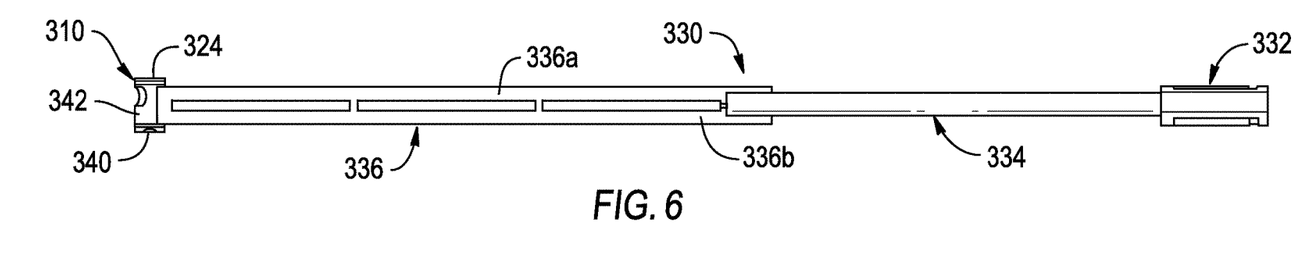
FIG. 6 is a side view of a drive assembly of the surgical loading unit of FIG. 2.

With reference to FIGS. 5 and 6, the surgical loading unit 300 includes a drive assembly 330 operatively associated with the end effector 304 and the drive mechanism (not shown) of the adapter assembly 200 and/or handle assembly 102. The drive assembly 330 includes a nut 332, a firing rod or tube 334, and a knife shaft 336 having the knife 310 disposed at a distal end thereof. The nut 332 extends proximally from the proximal body portion 302 of the surgical loading unit 300 through the outer tube 206 (FIG. 2) of the adapter assembly 200 and operably couples to the handle assembly 102 (FIG. 2), such that an actuation of the handle assembly 102 is configured to translate the nut 332. The firing rod 334 has a proximal end portion fixed to the nut 332 and a distal end portion fixed to a proximal end portion of the knife shaft 336. In embodiments, the nut 332 may be directly attached to the proximal end portion of the knife shaft 336 rather than be coupled via the firing rod 334. Since the knife shaft 336 is fixed to the nut 332, axial movement of the nut 332 through the outer tube 206 of the adapter assembly 20, in response to an actuation of the handle assembly 102, drives an axial movement of the knife shaft 336.

The knife shaft 336 has a lower portion 336b extending through a longitudinally-extending slot 338 defined in the anvil assembly 306, and an upper portion 336a extending through the longitudinally-extending slot 318 defined in the chassis 312 of the staple cartridge assembly 308. The knife shaft 336 of the drive assembly 330 has a distal end portion disposed within the surgical loading unit 300. The distal end portion of the knife shaft 336 has the knife 310 fixed thereto, which is configured to pivot the staple cartridge assembly 308 toward the anvil plate 306 during distal advancement of the knife 310.

As mentioned above, the knife 310 has an upper foot or plate 324 disposed outside of the chassis 312 of the staple cartridge assembly 308, a lower foot or plate 340 disposed within the slot 338 defined by the anvil assembly 306, and a sharp distally-oriented surface or blade 342 extending between and interconnecting the upper and lower plates 324, 340. The blade 342 is configured to sever tissue during distal advancement thereof through the end effector 304. The upper plate 324 of the knife 310 has a lower surface 324b in overlapping arrangement and, in some embodiments, in contact, with the outer surface 320 of the chassis 312.

In operation, to fire and clamp the end effector 304 of the surgical loading unit 300, the handle assembly 102 is actuated driving a translation of the drive assembly 330 in a distal direction. Given that the drive assembly 330, including the nut 332, the firing rod 334, and the knife shaft 336, is one integral unit, knife 310 advances distally through the anvil assembly 306 and the chassis 312 of the cartridge assembly 308 to pivot the chassis 312 toward the anvil assembly 306. As the knife 310 of the drive assembly 330 advances distally through the end effector 304, any tissue disposed therebetween is severed by the sharp, distally-oriented surface 342 of the knife 310. Also as the knife 310 advances toward the distal position, the actuation sled (not shown) is moved upwardly through the staple cartridge 316 to push the staples through the tissue and into engagement with the anvil assembly 306 to form the staples.

After a full actuation of the end effector 304, the drive assembly 330 is retracted back toward a starting position. As the knife 310 of the drive assembly 330 moves toward the proximal position, the upper plate 324 of the knife 310 passes underneath the inner peripheral surface 7 of the surgical port 2 due to the supports 322a, 322b of the chassis 312 maintaining the inner peripheral surface 7 of the surgical port 2 out of the knife's 310 path.

For a detailed description of the operation of an exemplary surgical loading unit, reference may be made to U.S. patent application Ser. No. 16/037,367, filed on Jul. 17, 2018, the entire contents of which being incorporated by reference herein.

Persons skilled in the art will understand that the adapter assemblies and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical loading unit, comprising:
an anvil assembly;
a staple cartridge assembly pivotably coupled to the anvil assembly, the staple cartridge assembly including:
a staple cartridge chassis defining a longitudinally-extending channel, the staple cartridge chassis having a support protruding outwardly from a proximal end thereof; and
a staple cartridge configured for receipt in the channel of the staple cartridge chassis; and
a knife including:
an upper plate coupled to the staple cartridge chassis and disposed outside of the channel, the upper plate having an upper surface and a lower surface; and
a lower plate coupled to the anvil assembly, the knife being configured to move from a proximal position toward a distal position to pivot the staple cartridge chassis toward the anvil assembly, wherein the support of the staple cartridge chassis has an upper surface that is coplanar with or above the upper surface of the upper plate when the knife is in the proximal position, wherein the support has a length substantially equal to a length of the knife.

2. The surgical loading unit according to claim 1, wherein the support of the staple cartridge chassis is disposed alongside the upper plate of the knife when the knife is in the proximal position.

3. The surgical loading unit according to claim 1, wherein the staple cartridge chassis defines a longitudinally-extending slot, the support of the staple cartridge chassis being disposed on both sides of the slot.

4. The surgical loading unit according to claim 1, wherein the support of the staple cartridge chassis is disposed alongside a first lateral side of the upper plate of the knife and a second lateral side of the upper plate of the knife when the knife is in the proximal position.

5. The surgical loading unit according to claim 1, wherein the upper surface of the support of the staple cartridge chassis is above the upper surface of the upper plate of the knife when the knife is in the proximal position.

6. The surgical loading unit according to claim 1, wherein the knife has a blade disposed between and interconnecting the upper and lower plates.

7. The surgical loading unit according to claim 1, wherein the support of the staple cartridge chassis is monolithically formed with the proximal end of the staple cartridge chassis.

8. A surgical system, comprising:
a surgical port defining a guide channel therethrough, the surgical port being configured to be positioned within a small incision in a patient; and
a surgical loading unit including:
an anvil assembly;
a staple cartridge assembly pivotably coupled to the anvil assembly, the staple cartridge assembly including:
a staple cartridge chassis defining a longitudinally-extending channel, the staple cartridge chassis having a support protruding outwardly from a proximal end thereof; and
a staple cartridge configured for receipt in the channel of the staple cartridge chassis; and
a knife including:
an upper plate coupled to the staple cartridge chassis and disposed outside of the channel, the upper plate having an upper surface and a lower surface; and
a lower plate coupled to the anvil assembly, the knife being configured to move from a proximal position toward a distal position to pivot the staple cartridge chassis toward the anvil assembly, wherein the support of the staple cartridge chassis has an upper surface that is coplanar with or above the upper surface of the upper plate of the knife when the knife is in the proximal position for expanding a portion of the guide channel of the surgical port out of a path of the knife, wherein the support extends alongside at least a majority of a length of the knife when the knife is in the proximal position.

9. The surgical system according to claim 8, wherein the support of the staple cartridge chassis is configured to contact and raise an inner peripheral surface of the surgical port to a position coplanar with or above the upper surface of the upper plate of the knife, such that the knife is configured to pass under the inner peripheral surface of the surgical port during movement to the proximal position.

10. The surgical system according to claim 8, wherein the support of the staple cartridge chassis is disposed alongside the upper plate when the knife is in the proximal position.

11. The surgical system according to claim 8, wherein the staple cartridge chassis defines a longitudinally-extending slot, the support of the staple cartridge chassis being disposed on both sides of the slot.

12. The surgical system according to claim 8, wherein the support of the staple cartridge chassis is disposed alongside a first lateral side of the upper plate of the knife and a second lateral side of the upper plate of the knife when the knife is in the proximal position.

13. The surgical system according to claim 8, wherein the upper surface of the support of the staple cartridge chassis is above the upper surface of the upper plate of the knife when the knife is in the proximal position.

14. The surgical system according to claim 8, wherein the knife has a blade disposed between and interconnecting the upper and lower plates.

15. The surgical system according to claim 8, wherein the support of the staple cartridge chassis is monolithically formed with the proximal end of the staple cartridge chassis.

\* \* \* \* \*